(12) United States Patent
Mulligan et al.

(10) Patent No.: US 11,646,116 B2
(45) Date of Patent: May 9, 2023

(54) INTELLIGENT IDENTIFICATION OF APPROPRIATE SECTIONS OF CLINICAL PRACTICAL GUIDELINE

(71) Applicant: INTERNATIONAL BUSINESS MACHINES CORPORATION, Armonk, NY (US)

(72) Inventors: Natalia Mulligan, Dublin (IE); Marco Luca Sbodio, Castaheany (IE); Alessandra Pascale, Castleknock (IE); Joao Bettencourt-Silva, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 128 days.

(21) Appl. No.: 16/362,487

(22) Filed: Mar. 22, 2019

(65) Prior Publication Data
US 2020/0303069 A1   Sep. 24, 2020

(51) Int. Cl.
*G16H 50/20*   (2018.01)
*G06N 20/00*   (2019.01)

(52) U.S. Cl.
CPC ............. *G16H 50/20* (2018.01); *G06N 20/00* (2019.01)

(58) Field of Classification Search
CPC ............................. G16H 50/20; G06N 20/00
USPC ............................................................ 705/2
See application file for complete search history.

(56) References Cited

U.S. PATENT DOCUMENTS

| | | | |
|---|---|---|---|
| 8,301,465 B2* | 10/2012 | Janas, III | G16H 70/20 705/2 |
| 8,515,887 B2 | 8/2013 | Lord et al. | |
| 10,957,449 B1* | 3/2021 | McNair | G16H 10/60 |
| 2005/0131741 A1 | 6/2005 | Tang et al. | |
| 2007/0175980 A1 | 8/2007 | Alsafadi | |
| 2008/0097965 A1* | 4/2008 | Alsafadi | G16H 70/20 715/764 |
| 2008/0312961 A1 | 12/2008 | Alsafadi | |
| 2011/0208540 A1 | 8/2011 | Lord et al. | |
| 2013/0030839 A1 | 1/2013 | Opfer et al. | |
| 2013/0151383 A1* | 6/2013 | Gancarz | G06Q 40/08 705/30 |
| 2013/0297340 A1 | 11/2013 | Van Zon et al. | |
| 2015/0006193 A1* | 1/2015 | Dadlani Mahtani | G16H 10/60 705/2 |

(Continued)

OTHER PUBLICATIONS

D. C. Stahl et al., "GDSI: a Web-based decision support system to facilitate the efficient and effective use of clinical practice guidelines," 37th Annual Hawaii International Conference on System Sciences, 2004. Proceedings of the, Big Island, HI, USA, 2004, pp. 10 pp.-, doi (Year: 2004).*

(Continued)

*Primary Examiner* — Robert W Morgan
*Assistant Examiner* — Bennett Stephen Erickson
(74) *Attorney, Agent, or Firm* — Griffiths & Seaton PLLC (57) ABSTRACT

A neural network is trained with patient historical data including features of patient pathways and labels characterizing a type of the patient pathways. During a runtime phase, the trained neural network matches a current patient profile with the patient historical data to extract selected portions of clinical practice guidelines (CPGs) identified according to one or more generated CPG models, the patient pathway models, and the current patient profile.

17 Claims, 7 Drawing Sheets

(56) References Cited

U.S. PATENT DOCUMENTS

| | | |
|---|---|---|
| 2015/0324543 A1 | 11/2015 | List et al. |
| 2016/0140300 A1* | 5/2016 | Purdie .................... G16H 10/60 |
| | | 705/2 |
| 2018/0307995 A1* | 10/2018 | Conroy .................. G06N 20/10 |
| 2019/0304603 A1* | 10/2019 | Takata ................... G06N 20/00 |
| 2019/0304604 A1* | 10/2019 | Kupersmith .......... G06F 16/903 |
| 2019/0355478 A1* | 11/2019 | Madhavan ............. A61N 5/103 |
| 2019/0362846 A1* | 11/2019 | Vodencarevic ........ G16H 50/30 |

OTHER PUBLICATIONS

F. Cossu et al., "Supporting Doctors through Mobile Multimodal Interaction and Process-Aware Execution of Clinical Guidelines," 2014 IEEE 7th International Conference on Service-Oriented Computing and Applications, Matsue, 2014, pp. 183-190, doi: 10.1109/SOCA.2014.44. (Year: 2014).*

D. C. Stahl et al., "GDSI: a Web-based decision support system to facilitate the efficient and effective use of clinical practice guidelines," 37th Annual Hawaii International Conference on System Sciences, 2004. Proceedings of the, Big Island, HI, 2004, pp. 10 pp.-, doi: 10. (Year: 2004).*

Anonymous, "OptCare—A system for personalizing clinical care pathways." IP.com Disclosure No. IPCOM000244976D, Publication Date: Feb. 4, 2016. (12 Pages).

\* cited by examiner

INTELLIGENT IDENTIFICATION OF APPROPRIATE SECTIONS OF CLINICAL PRACTICAL GUIDELINE

BACKGROUND OF THE INVENTION

Field of the Invention

The present invention relates in general to computing systems, and more particularly to, various embodiments for intelligent identification of appropriate sections of clinical practice guidelines by a processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize impacts on a well-being or health of a person.

SUMMARY OF THE INVENTION

Various embodiments for implementing intelligent clinical practice guidelines using one or more processors, are provided. In one embodiment, by way of example only, a method for implementing intelligent identification of appropriate sections of clinical practice guidelines, again by a processor, is provided. Selected portions of clinical practice guidelines (CPGs) may be identified according to one or more CPG models, patient pathway models, and current patient profile.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user such as, for example, a medical patient. For example, as the demand for and access to data continues to expand in society, consumers of information content, particularly individuals desiring to make well-informed decisions regarding a medical condition or health state, continue to increase. The openness of the internet with the ever-increasing availability of a variety of types of computing devices, IoT devices, and the cloud computing environment for viewing, interacting, or engaging with information, provides the ability of users to have continuous access to information content relating to a variety of settings.

For example, within the health care industry, clinical practice guidelines ("CPGs") may be used by various types of health professionals. In one aspect, evidence-based health care/medicine and evidence-based policies are approaches in the health care industry.

In one aspect, by way of example only, a CPG may be a set of recommendations, actions and goals that support physicians/health care professions making decisions to improve health service delivery and outcomes. In an additional aspect, a CPG may be statements that include recommendations intended to optimize user/patient care that are informed by a systematic review of evidence and an assessment of the benefits and harms of alternative care options. Thus, rather than dictating a one-size-fits-all approach to patient care, a CPG may offer an evaluation of a quality of relevant scientific literature, and an assessment of the likely benefits and harms of a particular treatment. This information enables health care clinicians to select a "best care" or "appropriate care" for a unique patient based on a patient preference.

The CPGs may also include any other evidence-based documents that describe a set of recommendations, instructions or tasks. For example, a local hospital protocol for management of patients with norovirus, a set of recommendations derived from the results of a clinical trial or a research paper with such similar information. A section of a CPG may refer to a particular recommendation or action described in the guideline. A CPG is a collection of multiple recommendations. For example: "measure blood pressure at least once every 12 months" is a recommendation of the Type 2 Diabetes guideline (NICE guideline NG28).

As used herein, the terms "Clinical Practice Guidelines," "Clinical Guidelines," "Guidelines," and "Clinical Pathways" may be used interchangeably. It should be noted, as used herein, the term "patient" may be used interchangeably with the terms "user." The patient profile may include a collection of historical data (e.g., electronic data from one or more electronic health care records) that may be related to one or more medical conditions of a user.

Effective CPG may be used, for example, to: 1) reduce disparities in healthcare delivery (e.g., there may be variabilities between regional and provider-level clinical care leading to poor outcomes and added costs that could be avoided by adhering to one or more CPGs, and 2) reduce the burden that health care professionals currently faces to stay current on, and adhere to, the increasing amounts of medical evidence. Adhering to a CPG may improve healthcare in theory, but guidelines may fail to address local constraints and knowledge (e.g., available in electronic health records (EHRs)). In case of a manual identification process, a use-case may include finding the CPGs describing a healthcare/well-being plan that a specific patient is following. However, such a process is extremely complex as it requires a perfect and complete knowledge of the patient, patient history, and/or other optimal/best clinical practice for all/any conditions. Given that such a perfect and complete knowledge of a patient and complete knowledge of CPGs is rare, only partial knowledge is usually provided or accessible for a patient. Moreover, even when a complete picture of a patient is provided, the coexistence of conditions (chronic and acute) can make the association to one or more sections of CPGs very time consuming and inaccurate. Furthermore, CPGs may include a large number of recommendations in an unstructured form and automatically identify sections of CPGs that are most appropriate for a given patient is currently difficult.

Accordingly, the present invention provides for implementing intelligent identification of appropriate sections of clinical practice guidelines, again by a processor, is provided. Selected portions of clinical practice guidelines (CPGs) may be identified for a user according to one or more CPG models and patient pathway models. A Patient Pathway may be a sequential (ordered) set of events and other information that may pertain to a specific condition. A pathway may be associated with at least one episode/encounter and a problem from a problem list. A patient pathway may include a start and end date, which may be the same as condition dates from the problem list. The patient pathway may include an inclusion criteria that may be any discrete event with a date within the patient pathway dates. In one aspect, the patient pathway may be structured into one or more segments. A patient pathway may be generated for each condition in a patient's problem list (e.g., list of all conditions).

In an additional aspect, various mechanisms of the illustrate embodiments provide for automatically identify one or more appropriate sections of CPGs that are appropriate for a patient by using automatically learned models of CPGs and patient pathways. The present invention may learn one or more patient pathway models (a "first model" or "M1") by processing historical data of patient profiles (e.g., structured data). The present invention may learn one or more clinical practice guidelines models (a "second model" or "M2") by processing a set existing CPG (textual data/unstructured data). The two models M1 and M2 (or a combination of the two models of patient pathway models and/or CPG model) may be used to compare/match a current patient profile of a current (e.g., new) patient to one or more CPGs. One or more patient pathways from the current patient may be extracted. The present invention may match the extracted patient pathways using the two models M1 and M2 and identifies one or more similar patient pathway and/or one or more sections of the one or more CPGs that are appropriate for those extracted patient pathways of the current patient. The present invention may produce/generate an ordered (ranked) list of sections of clinical practice guidelines that are most appropriate for all the pathways of the current patient. The present invention may use and/or analyze feedback data collected from one or more domain expert, patient profiles, historical feedback, or a combination thereof to (a) adjust/improve the quality of M2 (e.g., a CPG model), and (b) adjust/improve the matching of a current patient profile to one or more CPGs.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

In general, "best," "appropriate," and/or "optimize" may be used herein interchangeable and refer to and/or defined as "maximize," "minimize," or attain one or more specific targets, objectives, goals, or intentions. "Best," "appropriate," and/or "optimize" may also refer to maximizing a benefit to a user (e.g., maximize a health state/patient profile). "Best," "appropriate," and/or "optimize" may also refer to making the most effective or functional use of a situation, opportunity, or resource.

Additionally, "best," "appropriate," and/or "optimize" may need not refer to a best solution or result but may refer to a solution or result that "is good enough" for a particular application, for example. In some implementations, an objective is to suggest a "best" combination of sections of one or more CPGs, but there may be a variety of factors that may result in alternate suggestion of a combination of sections of one or more CPGs yielding better results. Thus, some changes to the variety of factors may result in a jump from one minimum/maximum to another minimum/maximum. In either case, resulting suggestions of a combination of sections of one or more CPGs may be considered "good enough," "substantially optimal," and/or "sufficiently good." Herein, the terms "best," "appropriate," and/or "optimize" may also refer to such results based on minima (or maxima, depending on what parameters are considered in the optimization problem) for suggesting of a combination of sections of CPGs.

In an additional aspect, the terms "optimize" and/or "optimizing" may refer to an operation performed in order to achieve an improved result such as reduced execution costs or increased resource utilization, whether or not the optimum result is actually achieved. Similarly, the term "optimize" may refer to a component for performing such an improvement operation, and the term "optimized" may be used to describe the result of such an improvement operation.

As used herein, so-called "appropriateness" or "inappropriateness" of sections of one or more CPGs associated with a current patient pathway may be subjective and context dependent. For example, one solution for an appropriate combination of sections of one or more CPGs associated with a current patient pathway may be interpreted and evaluated to be either satisfactory or unsatisfactory depending on one or more contextual factors. Accordingly, the so-called "appropriateness" of a particular combination of sections of one or more CPGs associated with a current patient pathway may depend greatly upon contextual factors, such as a patient profile (e.g., a user profile may include a collection of settings and/or information or attributes with a user such as, for example, gender, weight, age, etc.), environmental factors, social factors, religious factors, cultural factors, and other contextual factors. A deeper, cognitive analysis of the user and CPGs associated with a current patient pathway may be provided to further understand the user and/or interpret the appropriate combination of sections of one or more CPGs associated with a current patient pathway.

It should be noted that reference to calculating an 'interpreted appropriateness" against a predetermined threshold herein following may refer to implementations of a wide variety of metric analysis, data analytics, and other data processing as one of ordinary skill in the art will appreciate. For example, a predetermined threshold may be set as a numerical value, where certain kinds of sections of one or more CPGs associated with a current patient pathway are given certain weighted values, and an aggregate number of the weighted values may be compared against a numerical threshold value.

It should be noted as described herein, the term "cognitive" (or "cognition") may be relating to, being, or involving conscious intellectual activity such as, for example, thinking, reasoning, or remembering, that may be performed using a machine learning. In an additional aspect, cognitive or "cognition may be the mental process of knowing, including aspects such as awareness, perception, reasoning and judgment. A machine learning system may use artificial reasoning to interpret data from one or more data sources (e.g., sensor-based devices or other computing systems) and learn topics, concepts, and/or processes that may be determined and/or derived by machine learning.

In an additional aspect, cognitive or "cognition" may refer to a mental action or process of acquiring knowledge and understanding through thought, experience, and one or more senses using machine learning (which may include using sensor-based devices or other computing systems that include audio or video devices). Cognitive may also refer to identifying patterns of behavior, leading to a "learning" of one or more events, operations, or processes. Thus, the cognitive model may, over time, develop semantic labels to apply to observed behavior and use a knowledge domain or ontology to store the learned observed behavior. In one embodiment, the system provides for progressive levels of complexity in what may be learned from the one or more events, operations, or processes.

In additional aspect, the term cognitive may refer to a cognitive system. The cognitive system may be a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. A cognitive system may perform one or more computer-implemented cognitive operations that approximate a human thought process while enabling a user or a computing system to interact in a more natural manner. A cognitive system may comprise artificial intelligence logic, such as natural language processing (NLP) based logic, for example, and machine learning logic, which may be provided as specialized hardware, software executed on hardware, or any combination of specialized hardware and software executed on hardware. The logic of the cognitive system may implement the cognitive operation(s), examples of which include, but are not limited to, question answering, identification of related concepts within different portions of content in a corpus, and intelligent search algorithms, such as Internet web page searches.

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 1:
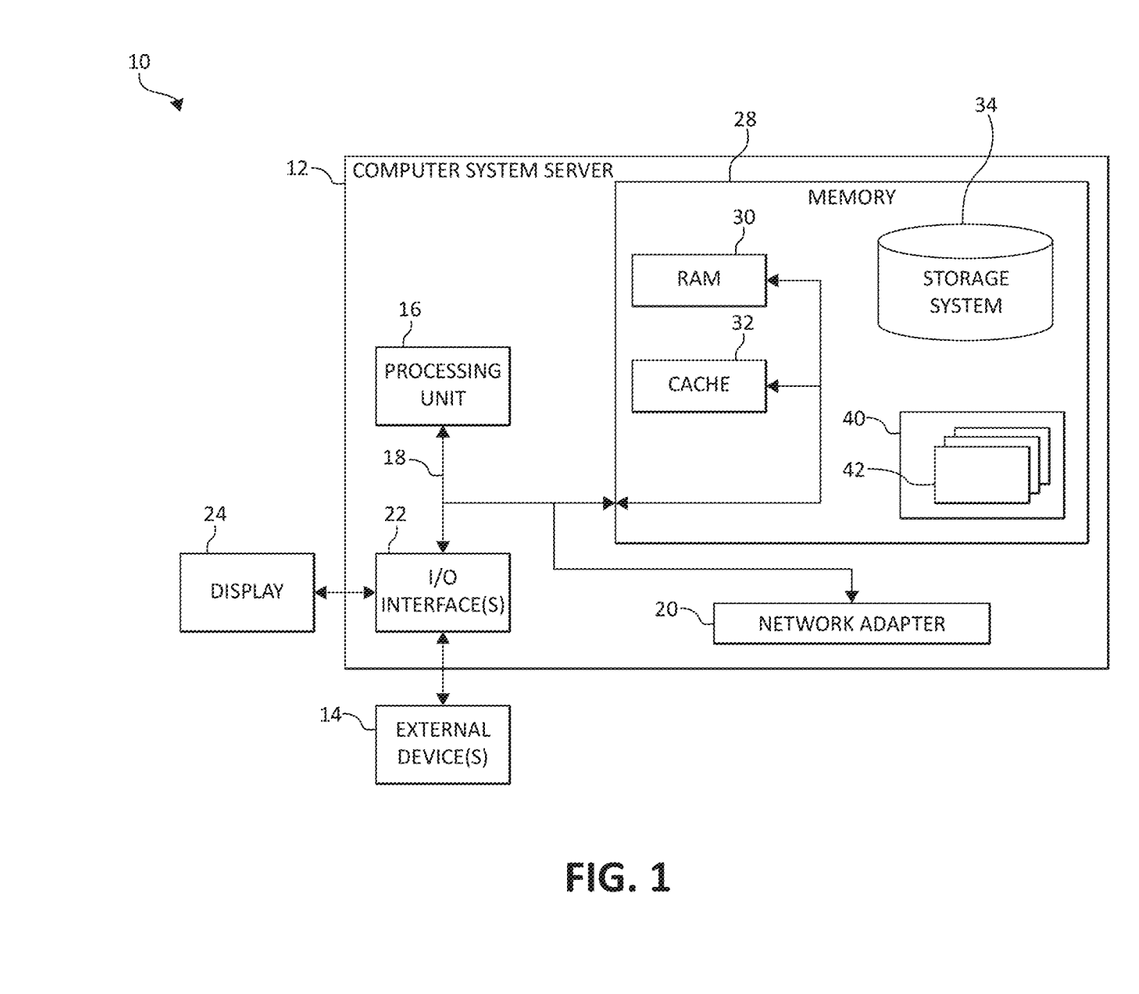
FIG. 1 is a block diagram depicting an exemplary computing node according to an embodiment of the present invention.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random-access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
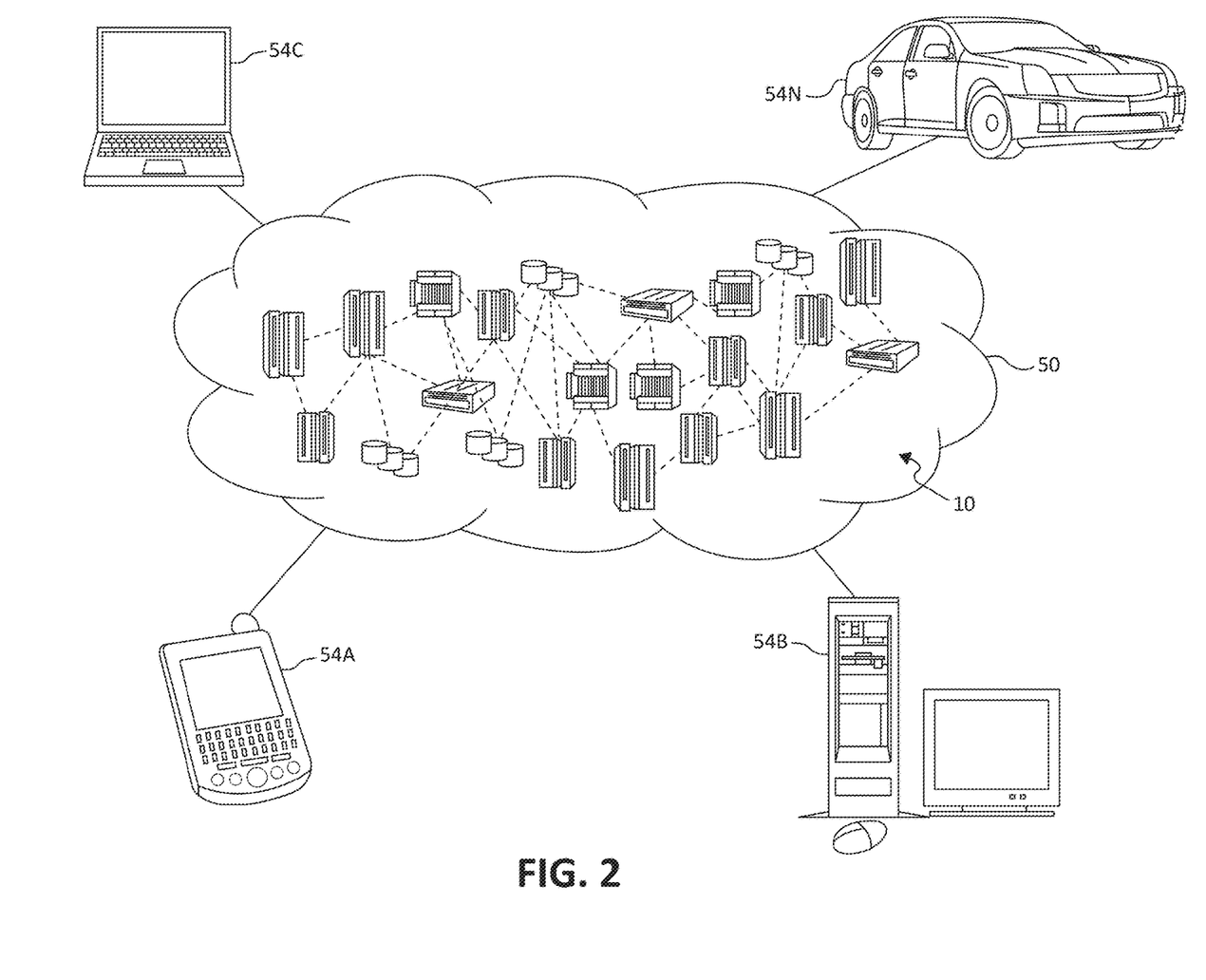
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
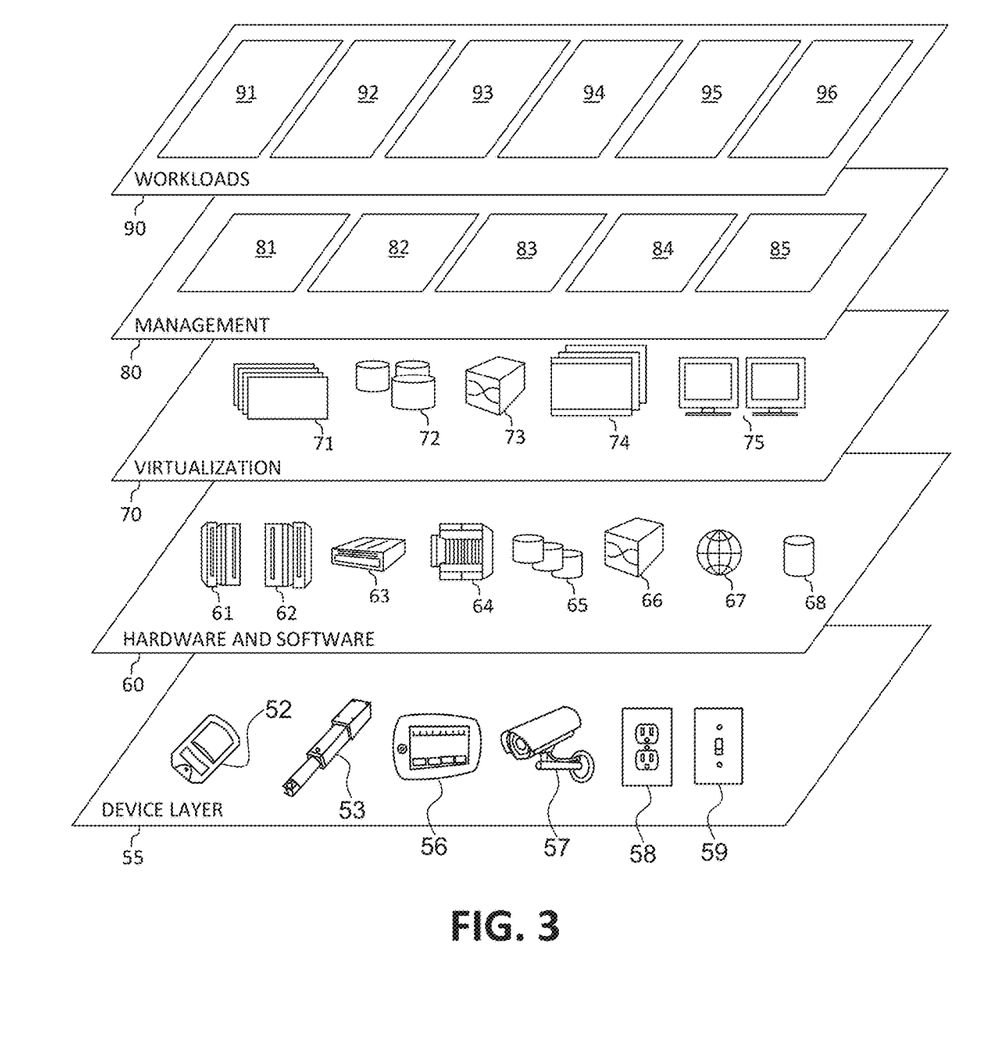
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances and a wide variety of other possible interconnected objects.

Hardware and software layer 60 may include hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent identification of appropriate sections of CPGs. In addition, workloads and functions 96 for intelligent identification of appropriate sections of CPGs may include such operations as data analytics, data analysis, and as will be further described, notification functionality. One of ordinary skill in the art will appreciate that the workloads and functions 96 for intelligent identification of appropriate sections of CPGs may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for the intelligent identification of appropriate sections of CPGs using one or more processors. One or more sections of one or more CPGs may be automatically identified for impacting a health state of a user according one or more learned CPG and patient pathway models. Thus, the present invention learns patient pathway features and matches/compares those learned patient pathway features to CPG features for intelligent identification of appropriate sections of CPGs.

That is, the present invention automatically learns features characterizing one or more sections of CPGs, thus enabling a fine-grained level of matching against a selected/current patient profile. The present invention may take as input one or more CPGs in textual format, without requiring the CPGs to have a specific logical or rule-based structure. The present invention provides the ability to automatically identify the most appropriate sections of CPGs for a patient by using automatically learned models of CPGs and patient pathways. The present invention may use one or more ML models for identifying the most appropriate sections of clinical guidelines that apply to a given patient.

Figure 4:
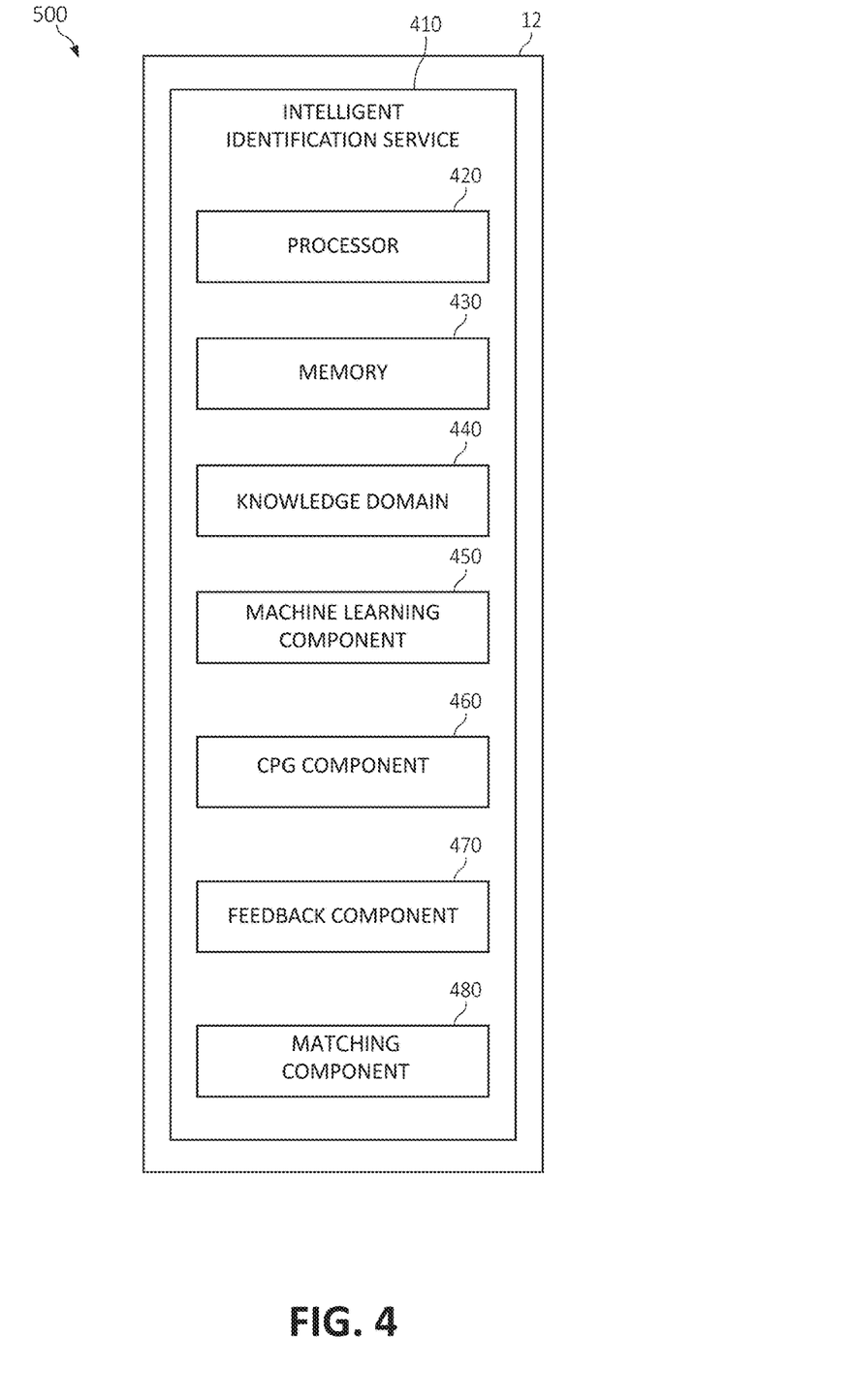
FIG. 4 is an additional block diagram depicting an exemplary functional relationship between various aspects of the present invention.

Turning now to FIG. 4, a block diagram depicting exemplary functional components 400 according to various mechanisms of the illustrated embodiments is shown. FIG. 4 illustrates intelligent identification of appropriate sections of CPGs workloads and functions and training of a machine-learning model in a computing environment, such as a computing environment 402, according to an example of the present technology. As will be seen, many of the functional blocks may also be considered "modules" or "components" of functionality, in the same descriptive sense as has been previously described in FIGS. 1-3.

With the foregoing in mind, the module/component blocks of computing system 400 may also be incorporated into various hardware and software components of a system for intelligent identification of appropriate sections of CPGs in accordance with the present invention. Many of the functional blocks 400 may execute as background processes on various components, either in distributed computing components, or on the user device, or elsewhere.

An intelligent identification system 410 is shown, incorporating processing unit 420 ("processor") to perform various computational, data processing and other functionality in accordance with various aspects of the present invention. The intelligent identification system 410 may be provided by the computer system/server 12 of FIG. 1. The processing unit 420 may be in communication with memory 430. The intelligent identification system 410 may also include a knowledge domain 440, machine learning component 450, a feedback component 470, a matching component 480.

In one aspect, the intelligent identification system 410 may provide virtualized computing services (i.e., virtualized computing, virtualized storage, virtualized networking, etc.). More specifically, the intelligent identification system 410 may provide virtualized computing, virtualized storage, virtualized networking and other virtualized services that are executing on a hardware substrate.

In one aspect, the knowledge domain 440 may be a database, which may also be an ontology of concepts representing a domain of knowledge. A thesaurus or ontology may be included in the knowledge domain 440 and may also be used to identify languages (types and rules relating to the language), grammar rules/policies, syntax rules, speech patterns, semantic relationships, and cultural speech patterns/rules/customers, and/or various dialects of a particular region. In one aspect, the term "domain" is a term intended to have its ordinary meaning. In addition, the term "domain" may include an area of expertise for a system or a collection of material, information, content and/or other resources related to a particular subject or subjects. A domain can refer to information related to any particular subject matter or a combination of selected subjects.

The term ontology is also a term intended to have its ordinary meaning. In one aspect, the term ontology in its broadest sense may include anything that can be modeled as an ontology, including but not limited to, taxonomies, thesauri, vocabularies, and the like. For example, an ontology may include information or content relevant to a domain of interest or content of a particular class or concept. The ontology can be continuously updated with the information synchronized with the sources, adding information from the sources to the ontology as models, attributes of models, or associations between models within the ontology.

Additionally, the domain knowledge may include one or more external resources such as, for example, links to one or more Internet domains, webpages, and the like. Additionally, the knowledge domain 440 may include data that may be received, updated, and/or communicated in real-time to and/or from one or more domain experts. For example, the feedback component 470 may receive real-time feedback from one or more domain experts and the feedback data may be maintained, stored, and/or updated in the knowledge domain 440.

In one aspect, the matching component 480 may identify and/or match selected portions of one or more CPGs to a select user (e.g., patient) according to one or more CPG models and one or more patient pathway models.

The CPG component 460, in association with the machine learning component 450, may learn the one or more CPG models using a set of CPGs. The CPG component 460, in association with the machine learning component 450, may also learn the patient pathway models from collected data from a plurality of patient profiles, which may be included, stored, and maintained in the knowledge domain 440. That is, the machine learning component 450 may be initialized to learn and/or assist in learning the one or more CPG models (e.g., "M2") and patient pathway models (e.g., "M1"). That is, machine learning component 450 may learn a patient pathway model ("M1") using historical data of structured data, and learn a CPG model (e.g., "M2") using unstructured data.

The matching component 480 may identify and/or match a profile of a user to one or more selected portions of the CPGs according to the patient pathway model (e.g., "M1") and the CPG model (e.g., "M2"). The matching component 480 may rank a list of the selected portions of the CPGs for a plurality of patient pathways for the user.

The feedback component 470 may collect and use feedback data to adjust the one or more CPG models and assist with a machine learning operation. The machine learning component 450 may use the knowledge domain 440 to use and/or analyze feedback data collected from one or more domain experts, patient profiles, historical feedback, or a combination thereof to (a) adjust/improve the quality CPG model, and (b) adjust/improve the matching of a current patient profile to one or more sections of CPGs.

In one aspect, the various machine learning operations of the machine learning component 450, as described herein, may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, backpropagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are within the scope of this disclosure. Also, when deploying one or more machine learning models, a computing device may be first tested in a controlled environment before being deployed in a public setting. Also even when deployed in a public environment (e.g., external to the controlled, testing environment), the computing devices may be monitored for compliance.

In one aspect, the intelligent identification system 410 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.) Thus, as used herein, a calculation operation may include all or part of the one or more mathematical operations.

Figure 5:
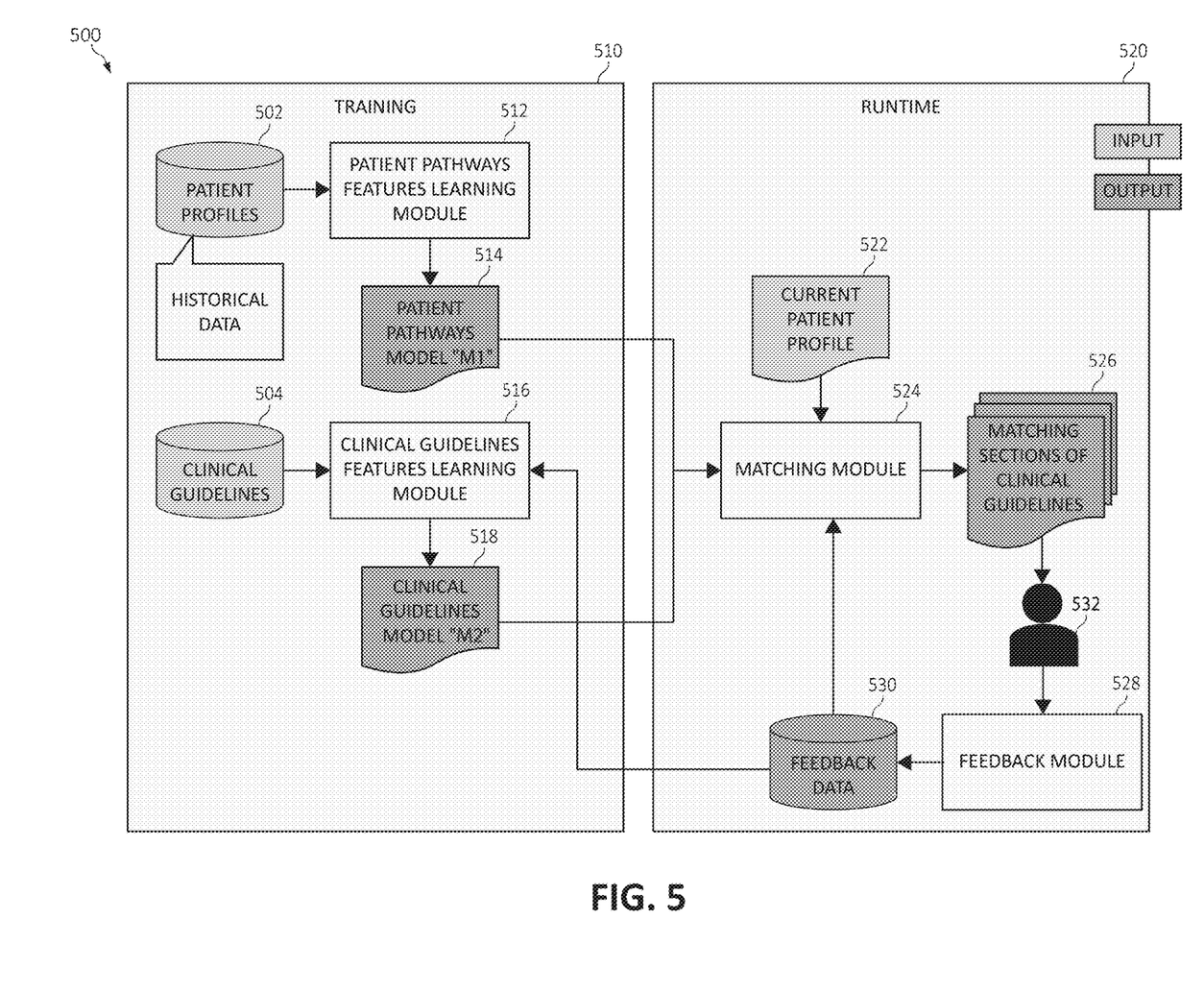
FIG. 5 is an additional block diagram depicting intelligent identification of appropriate sections of clinical practice guidelines in which aspects of the present invention may be realized.

Turning now to FIG. 5, a block diagram of exemplary functionality 500 of an intelligent identification of appropriate sections of CPGs is depicted. As will be seen, many of the functional blocks may also be considered "modules" or "components" of functionality, in the same descriptive sense as has been previously described in FIGS. 1-3.

As shown, the various blocks of functionality are depicted with arrows designating the blocks' 500 relationships with each other and to show process flow of an intelligent identification of appropriate sections of CPGs. Additionally, descriptive information is also seen relating each of the functional blocks 500. As will be seen, many of the functional blocks may also be considered "modules" or "components" of functionality, in the same descriptive sense as has been previously described in FIGS. 1-5. With the foregoing in mind, the module blocks 500 may also be incorporated into various hardware and software components of a system for image enhancement in accordance with the present invention. Many of the functional blocks 500 may execute as background processes on various components, either in distributed computing components, or on the user device, or elsewhere, and generally unaware to the user performing generalized tasks of the present invention.

As illustrated, the operations for intelligent identification of appropriate sections of CPGs may include a training phase 510 and a runtime phase 520.

Starting with block 502, during the training phase, a patient profile may be accessed for a patient having historical data associated therewith. That is, block 502 may include a database with a selected number of historical patient profiles data. The patient profile may be sent to a patient pathways features learning module 512 and used as input. The patient pathways features learning module 512 may learn (and produce as output) one or more models of patient pathways (e.g., patient pathway model "M1"), as in block 514. That is, the patient pathways features learning module 512 may initialize a machine learning operation and implement one or more machine learning operations to learn features of one or more patient pathways. In one aspect, the patient pathways are extracted as an ordered sequence of events from the historical patient profiles data. A neural network may be trained using labelled data that may include 1) a vector representation of patient pathways, and/or 2) labels characterizing the type of pathways. One or more learned patient pathway models may be sent to the matching module 524, for commencing the runtime phase 520.

Additionally, during the training phase 510, a collection of clinical guidelines 504 and/or feedback data 530 (if available from the runtime phase 520) may be sent to the clinical guidelines features learning module 516 and used as input. The clinical guidelines features learning module 516 may learn (and produce as output) one or more clinical guidelines models (e.g., CPG models or clinical guideline model "M2"), as in block 518. In one aspect, the CPGs may be available as documents (e.g., textual data). The clinical guidelines features learning module 516 may build a quantitative representation of each of the features of guidelines. In one embodiment, clinical guidelines features learning module 516 may use artificial intelligence, natural language processing ("NLP), and/or one or more word embedding operations, which yield a vector-based model of the text. Additionally, the clinical guidelines features learning module 516 may use feedback data 530 from one or more domain experts 532 to improve the quality of the learned CPG model. The feedback data 530 may be used as labelled data at training time. The clinical guidelines features learning module 516 may send the one or more models of clinical guidelines (e.g., CPG models or clinical guideline model "M2") to the matching module 524.

In one aspect, the matching module 524 may use as input the patient pathways model M1 (computed during the training phase) and the clinical guidelines model M2 (computed during the training phase). Data from a current patient profile 522 and/or feedback data 530, if available, may also be accessed and used by the matching module 524.

The matching module 524 may compare the data and provide a sorted list of sections of clinical guidelines matching the current patient profile 522. That is, the matching module 524 extracts a patient pathway from the current patient profile 522. For each patient pathway "H", the current patient profile 522 uses the patient pathways model M1 to build a vector representation of patient pathway H. The matching module 524 may determine and/or compute one or more similarity metrics between the vector representation of the patient pathway H and vector representations of the guidelines in clinical guideline model M2. The similarity metric provides a sorted list of sections of guidelines/CPGs that are closest to the patient pathway H. The sections of guidelines/CPGs that are the closest/most similar are the most appropriate/determined section for patient pathway H. If available, the present invention may use the feedback data 530 collected from the domain expert(s) 532 via a feedback module 528 to improve the ranking in the sorted list.

The feedback module 528 may receive as input data from one or more domain experts such as, for example, the domain expert 532, and provide feedback data 530 on the output produced by the matching module 524. That is, the feedback module 528 may provide a structured database of feedbacks. The feedback module 528 allows for users to provide feedback about the matching sections of CPGs using one or more selected/defined user interfaces of a computing system. In one embodiment, the feedback may include, for example, an upvote/downvote to represent agreement/disagreement. The feedback data 530 may also be communicated back to the clinical guidelines features learning module 516 and to the matching module 524.

Figure 6:
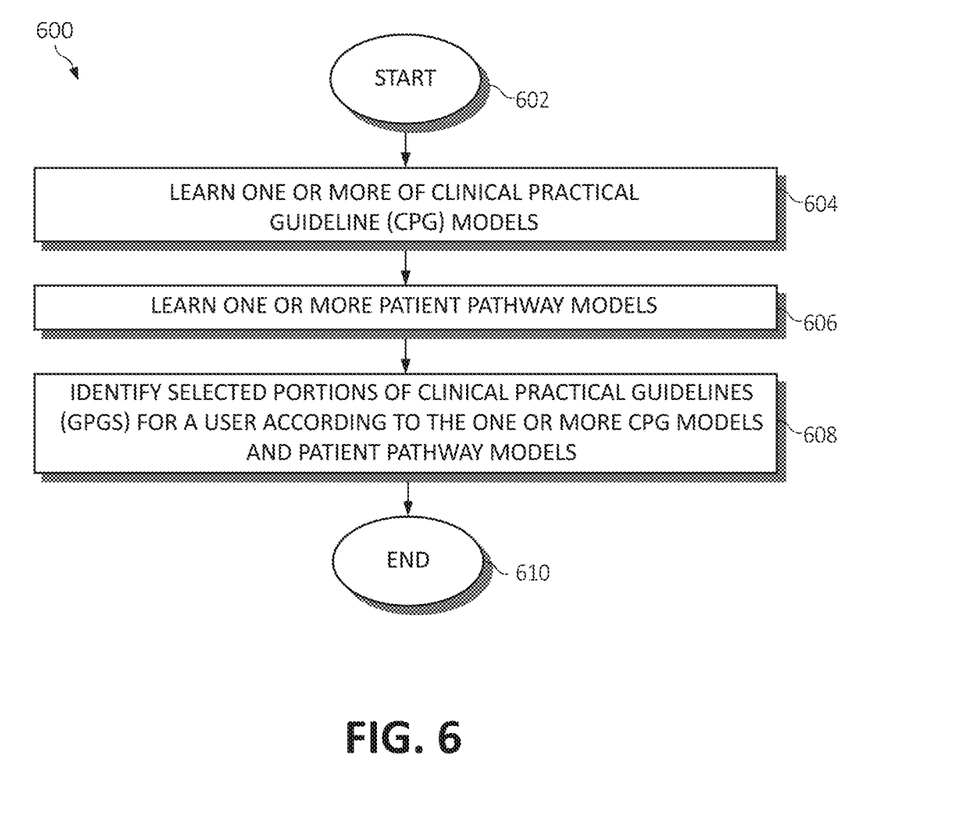
FIG. 6 is an additional flowchart diagram depicting an additional exemplary method for implementing intelligent identification of appropriate sections of clinical practice guidelines in which aspects of the present invention may be realized.

Turning now to FIG. 6, a method 600 for implementing intelligent identification of appropriate sections of clinical practice guidelines by a processor is depicted, in which various aspects of the illustrated embodiments may be implemented. The functionality 600 may be implemented as a method executed as instructions on a machine, where the instructions are included on at least one computer readable medium or one non-transitory machine-readable storage medium. The functionality 600 may start in block 602.

One or more CPG models may be learned, as in block 604. One or more patient pathway models may be learned, as in block 606. Selected portions of clinical practice guidelines (CPGs) may be identified for a user according to the one or more CPG models and patient pathway models, as in block 608. The functionality 600 may end, as in block 610.

Figure 7:
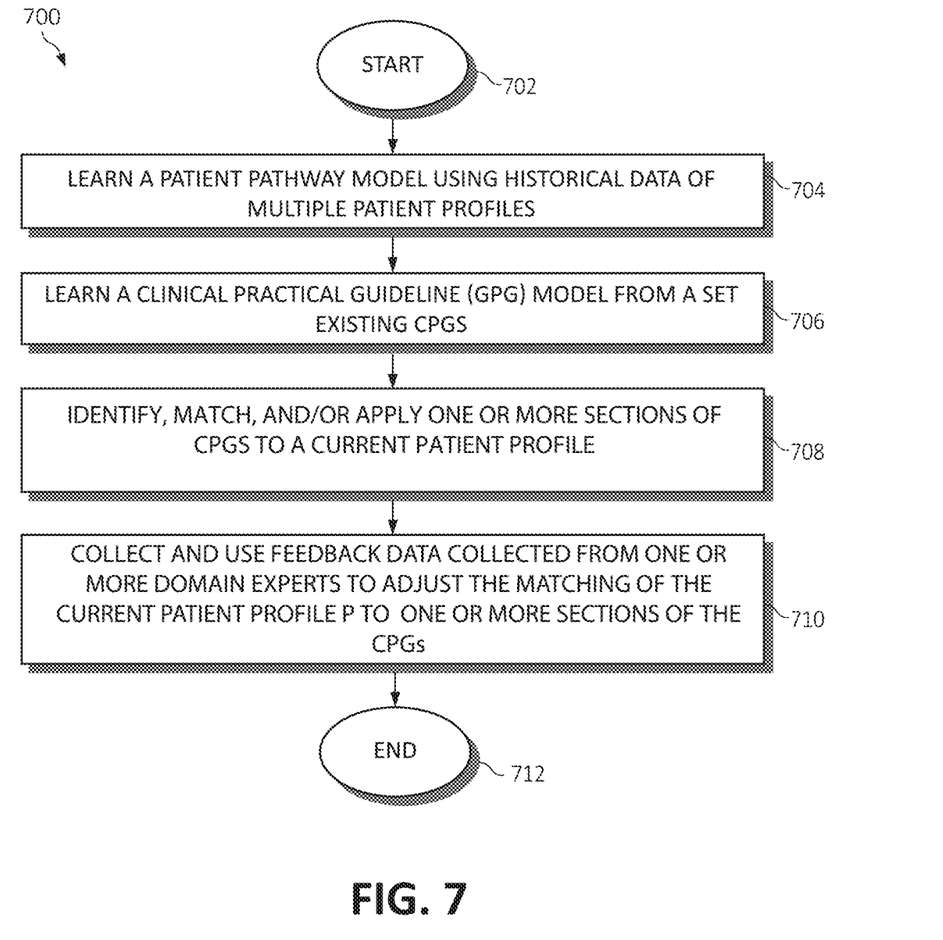
FIG. 7 is an additional flowchart diagram depicting an additional exemplary method for implementing intelligent identification of appropriate sections of clinical practice guidelines by a processor, again in which aspects of the present invention may be realized.

Turning now to FIG. 7, a method 700 for implementing intelligent identification of appropriate sections of clinical practice guidelines by a processor is depicted, in which various aspects of the illustrated embodiments may be implemented. The functionality 700 may be implemented as a method executed as instructions on a machine, where the instructions are included on at least one computer readable medium or one non-transitory machine-readable storage medium. The functionality 700 may start in block 702.

A patient pathway model may be learned using historical data of multiple patient profiles, as in block 704. A CPG model may be learned from a set existing CPGs, as in block 706. The patient pathway model and CPG model may be used to identify, match, and/or apply one or more sections of CPGS to a current patient profile of a current user, as in block 708. Feedback data may be used and collected from one or more domain experts to adjust the matching of the current patient profile to one or more sections of the CPGs (and also adjust the one or more CPGs), as in block 710. The functionality 700 may end, as in block 712.

In one aspect, in conjunction with and/or as part of at least one block of FIGS. 6-7, the operations of methods 600 and/or 700 may include each of the following. The operations of methods 600 and/or 700 learn a patient pathway model using historical data of structured data, learn a CPG model using unstructured data (e.g., text data and/or existing CPG models, and/or match a profile of the user to the selected portions of the CPGs according to the patient pathway model and the CPG model.

The operations of methods 600 and/or 700 may rank a list of the selected portions of the CPGs for a plurality of patient pathways for the user. The operations of methods 600 and/or 700 may initialize a machine learning mechanism to learn the one or more CPG models and patient pathway models. The operations of methods 600 and/or 700 may collect and use feedback data to adjust or apply to the one or more CPG models and assist with a machine learning operation.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for implementing intelligent clinical practice guidelines by a processor, comprising:
receiving, from a database, a patient profile having historical data associated with a patient and a collection of clinical practice guidelines (CPGs), wherein features of one or more patient pathways are extracted as an ordered sequence of medical events associated with the patient from the historical data of the patient profile;
training an artificial neural network, in a first training phase under a supervised artificial intelligence-based machine learning operation, using a vector representation of the features extracted from the one or more patient pathways and labels characterizing a type of the one or more patient pathways;
generating, according to the first training phase, a first model comprising one or more patient pathway models using the historical data containing only structured data stored in the database;
training the artificial neural network, in a second training phase under the supervised artificial intelligence-based machine learning operation, using the collection of CPGs inclusive of vector representations of features extracted from the collection of CPGs;

generating, discretely from the first model and according to the second training phase, a second model comprising one or more CPG models using only unstructured data stored in the database and at least one external source;

performing a comparison of similarity metrics between vector representations of an output of the first model and an output of the second model, wherein performing the comparison includes:

generating, from the output of the first model, the vector representations of only structured text of the one or more patient pathways from one of a plurality of patient profiles, generating, from the output of the second model, the vector representations of only unstructured text of the collection of CPGs, and comparing the one of the plurality of patient profiles, the one or more patient pathways, and the collection of CPGs using the vector representations of only the structured text and the vector representations of only the unstructured text while identifying the similarity metrics determined from the comparison; and identifying, during a runtime phase under the supervised artificial intelligence-based machine learning operation, selected portions of the CPGs according to matches determined from the comparison, wherein a sorted list of those of the selected portions of the CPGs describing potential treatments not yet administered to a new patient and being most similar to the ordered sequence of medical events of the one of more patient pathways is provided as output.

2. The method of claim 1, further including learning the one or more CPG models using a set of the CPGs.

3. The method of claim 1, wherein the database includes the plurality of patient profiles, and further including learning the one or more patient pathway models from collected data from the plurality of patient profiles.

4. The method of claim 1, further including matching a profile to the selected portions of the CPGs according to the patient pathway model and the CPG model.

5. The method of claim 1, further including ranking the sorted list of the selected portions of the CPGs for a plurality of patient pathways according to feedback data.

6. The method of claim 1, further including collecting and using feedback data to adjust or apply to the one or more CPG models and assist in training the neural network.

7. A system for implementing intelligent clinical practice guidelines, comprising:

one or more computers with executable instructions that when executed cause the system to:

identify, from a database, a patient profile having historical data associated with a patient and a collection of clinical practice guidelines (CPGs), wherein features of one or more patient pathways are extracted as an ordered sequence of medical events associated with the patient from the historical data of the patient profile;

train an artificial neural network, in a first training phase under a supervised artificial intelligence-based machine learning operation, using a vector representation of the features extracted from the one or more patient pathways and labels characterizing a type of the one or more patient pathways;

generate, according to the first training phase, a first model comprising one or more patient pathway models using the historical data containing only structured data stored in the database;

train the artificial neural network, in a second training phase under the supervised artificial intelligence-based machine learning operation, using the collection of CPGs inclusive of vector representations of features extracted from the collection of CPGs;

generate, discretely from the first model and according to the second training phase, a second model comprising one or more CPG models using only unstructured data stored in the database and at least one external source;

perform a comparison of similarity metrics between vector representations of an output of the first model and an output of the second model, wherein performing the comparison includes:

generating, from the output of the first model, the vector representations of only structured text of the one or more patient pathways from one of a plurality of patient profiles, generating, from the output of the second model, the vector representations of only unstructured text of the collection of CPGs, and comparing the one of the plurality of patient profiles, the one or more patient pathways, and the collection of CPGs using the vector representations of only the structured text and the vector representations of only the unstructured text while identifying the similarity metrics determined from the comparison; and identify, during a runtime phase under the supervised artificial intelligence-based machine learning operation, selected portions of the CPGs according to matches determined from the comparison, wherein a sorted list of those of the selected portions of the CPGs describing potential treatments not yet administered to a new patient and being most similar to the ordered sequence of medical events of the one of more patient pathways is provided as output.

8. The system of claim 7, wherein the executable instructions further learn the one or more CPG models using a set of the CPGs.

9. The system of claim 7, wherein the database includes the plurality of patient profiles, and wherein the executable instructions further learn the one or more patient pathway models from collected data from the plurality of patient profiles.

10. The system of claim 7, wherein the executable instructions further match a profile to the selected portions of the CPGs according to the patient pathway model and the CPG model.

11. The system of claim 7, wherein the executable instructions further rank the sorted list of the selected portions of the CPGs for a plurality of patient pathways according to feedback data.

12. The system of claim 7, wherein the executable instructions further collect and use feedback data to adjust or apply to the one or more CPG models and assist in training the neural network.

13. A computer program product for implementing intelligent clinical practice guidelines by a processor, the computer program product comprising a non-transitory computer-readable storage medium having computer-readable program code portions stored therein, the computer-readable program code portions comprising:

an executable portion that receives, from a database, a patient profile having historical data associated with a patient and a collection of clinical practice guidelines (CPGs), wherein features of one or more patient pathways are extracted as an ordered sequence of medical events associated with the patient from the historical data of the patient profile;

an executable portion that trains an artificial neural network, in a first training phase under a supervised artificial intelligence-based machine learning operation, using a vector representation of the features extracted from the one or more patient pathways and labels characterizing a type of the one or more patient pathways;

an executable portion that generates, according to the first training phase, a first model comprising one or more patient pathway models using the historical data containing only structured data stored in the database;

an executable portion that trains the artificial neural network, in a second training phase under the supervised artificial intelligence-based machine learning operation, using the collection of CPGs inclusive of vector representations of features extracted from the collection of CPGs;

an executable portion that generates, discretely from the first model and according to the second training phase, a second model comprising one or more CPG models using only unstructured data stored in the database and at least one external source;

performing a comparison of similarity metrics between vector representations of an output of the first model and an output of the second model, wherein performing the comparison includes:

generating, from the output of the first model, the vector representations of only structured text of the one or more patient pathways from one of a plurality of patient profiles, generating, from the output of the second model, the vector representations of only unstructured text of the collection of CPGs, and comparing the one of the plurality of patient profiles, the one or more patient pathways, and the collection of CPGs using the vector representations of only the structured text and the vector representations of only the unstructured text while identifying the similarity metrics determined from the comparison; and an executable portion that identifies, during a runtime phase under the supervised artificial intelligence-based machine learning operation, selected portions of the CPGs according to matches determined from the comparison, wherein a sorted list of those of the selected portions of the CPGs describing potential treatments not yet administered to a new patient and being most similar to the ordered sequence of medical events of the one of more patient pathways is provided as output.

14. The computer program product of claim 13, wherein the database includes the plurality of patient profiles, and further including an executable portion that:

learns the one or more CPG models using a set of the CPGs; or learns the one or more patient pathway models from collected data from the plurality of patient profiles.

15. The computer program product of claim 13, further including an executable portion that matches a profile to the selected portions of the CPGs according to the patient pathway model and the CPG model.

16. The computer program product of claim 13, further including an executable portion that ranks the sorted list of the selected portions of the CPGs for a plurality of patient pathways according to feedback data.

17. The computer program product of claim 13, further including an executable portion that collects and uses feedback data to adjust or apply to the one or more CPG models and assist in training the neural network.

* * * * *